United States Patent [19]

Green et al.

[11] 3,968,132

[45] July 6, 1976

[54] (17R)-SPIRO-[ANDROSTANE-17,1'-CYCLOBUTAN]-2'-ONES, METHODS FOR THEIR MANUFACTURE AND INTERMEDIATES USEFUL THEREIN

[75] Inventors: Michael J. Green, New Brunswick; Ho-Jane Shue, Belleville, both of N.J.

[73] Assignee: Schering Corporation, Kenilworth, N.J.

[22] Filed: Dec. 23, 1974

[21] Appl. No.: 535,387

[52] U.S. Cl............................ 260/397.3; 260/397.4; 260/397.45; 260/239.57
[51] Int. Cl.² ........................................... C07J 5/00
[58] Field of Search..................... 260/397.3, 397.4; /Machine Searched Steroids

[56] References Cited
UNITED STATES PATENTS 3,657,288   4/1972   Wiechert ....................... 260/397.3

*Primary Examiner*—Elbert L. Roberts
*Attorney, Agent, or Firm*—Mary S. King

[57] ABSTRACT

(17R)-Spiro-[androstane-17,1'-cyclobutan]-2'-ones are prepared by the reaction of a 17-oxo androstane, wherein all other ketones are blocked, with a cyclopropylarylsulfide or with a cyclopropylarylsulfonium salt having a non-nucleophilic anion, in an organic solvent together with a strong base, followed by reaction in situ of the intermediate thereby formed with aqueous acid or water.

Some (17R)-spiro-[androstan-17,1'-cyclobutan]-2'-ones are useful as intermediates in preparing (17R)-spiro-[3-oxo-4-androstene-17,1'-cyclobutan]-2'-ones which are aldosterone antagonists. Additionally, (17R)-spiro-[androstane-17,1'-cyclobutan]-2'-ones are useful as intermediates in preparing known 17α-pregnane-21,17β-carbolactones, valuable aldosterone blocking agents.

23 Claims, No Drawings

(17R)-SPIRO-[ANDROSTANE-17,1'-CYCLOBUTAN]-2'-ONES, METHODS FOR THEIR MANUFACTURE AND INTERMEDIATES USEFUL THEREIN

FIELD OF INVENTION

This invention relates to novel steroidal compositons-of-matter, to methods for their manufacture and intermediates useful therein.

More specifically, this invention relates to novel (17R)-spiro-[androstane-17,1'-cyclobutan]-2'-ones valuable as intermediates and as aldosterone antagonists, to methods for their manufacture and intermediates useful therein.

PRIOR ART

Known in the art (e.g. U.S. Pat. No. 3,657,288) are (17S)-spiro-[androstane-17,1'-cyclobutan]-2'-ones and the 3'-one isomers thereof, and the process for their preparation by the reaction of a 17α-halogeno-20-oxo-21-unsubstituted pregnane with dimethylmethylene sulfonium oxide. The (17S)-spiro-[androstane-17,1'-cyclobutan]-2'-ones and isomeric 3'-ones are described as possessing anti-androgenic and oral contraceptive activities and as intermediates which, upon treatment with a percarboxylic acid, are convertible to the corresponding 17β-pregnane-21,17α-carbolactones.

Unknown in the art are (17R)-spiro-[androstane-17,1'-cyclobutan]-2'-ones or a method for their manufacture.

By this invention, (17R)-spiro-[androstane-17,1'-cyclobutan]-2'-ones have been discovered and a novel method for their preparation. It has also been discovered that the (17R)-spiro-[androstane-17,1'-cyclobutan]-2'-ones are useful as intermediates in preparing 17α-pregnane-21,17β-carbolactones, known aldosterone antagonists and, additionally, that the (17R)-spiro-[3-oxo-4-androsten-17,1'-cyclobutan]-2'-ones of this invention are aldosterone antagonists per se.

GENERAL DESCRIPTION OF THE INVENTION COMPOSITION-OF-MATTER ASPECT

Included among the aldosterone blocking agents of this invention are steroids selected from the group consisting of a 3-oxo-4-androstene-17-spirocyclobutanone of the following formula I:

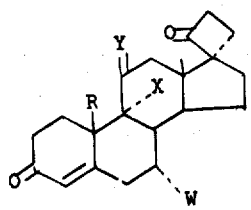

wherein R is a member selected from the group consisting of hydrogen and methyl; and
W is a member selected from the group consisting of hydrogen and acetylthio;
X and Y are both hydrogen, or X is fluorine and Y is (H,βOH) provided R is methyl;
the 1-dehydro analogs thereof when R is methyl;
the 6-dehydro analogs thereof when W is hydrogen;
the 1,6-bis-dehydro analogs thereof when R is methyl and W is hydrogen;
and a 3-oxo-4-androstene-17-spirocyclobutanone of the following formula II:

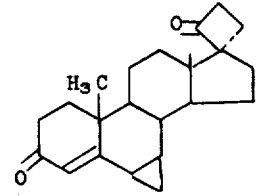

and the 1-dehydro analog thereof.

Typical aldosterone blocking agents of this invention thus include compounds of formula I such as:
(17R)-spiro-[4-androstene-17,1'-cyclobutane]-3,2'-dione (formula I, R is methyl, W, X and Y are hydrogen), the 6-dehydro, 1-dehydro and 1,6-bis-dehydro analogs thereof, and the 9α-fluoro-11β-hydroxy derivatives of the foregoing (i.e. compounds of formula I wherein R is methyl, W is hydrogen, X is fluorine and Y is (H,βOH));
(17R)-spiro-[19-nor-4-androstene-17,1'-cyclobutane]-3,2'-dione (formula I, R, W, X and Y are hydrogen), and the 6-dehydro analog thereof;
(17R)-spiro-[7α-thioacetyl-4-androstene-17,1'-cyclobutane]-3,2'-dione (formula I, R is methyl, X and Y are hydrogen and W is thioacetyl), the 1-dehydro analog thereof and the 9α-fluoro-11β-hydroxy derivatives of the foregoing (i.e. compounds of formula I wherein R is methyl, X is fluorine, Y is (H,βOH) and W is thioacetyl);
(17R)-spiro-[7α-thioacetyl-19-nor-4-androstene-17,1'-cyclobutane]-3,2'-dione (formula I, R, X and Y are hydrogen and W is thioacetyl); and
(17R)-spiro-[6β,7β-cyclomethylene-4-androstene-17,1'-cyclobutane]-3,2'-dione (formula II) and the 1-dehydro analog thereof.

The 3-oxo-4-androstene-17-spirobutanones of formulae I and II exhibit aldosterone antagonist activity as demonstrated by tests in the desoxycorticosterone treated adrenalectomised rat when administered subcutaneously by the method of Kagawa as described by C. M. Kagawa, Endocrinology 67, 125 (1960), in C. M. Kagawa and E. A. Brown, Proc. Sec. Exptl. Biol. Med. 105, 648 (1960) and C. M. Kagawa in "Methods in Hormone Research", R. I. Dorfman Ed., Vol. III, 351–414 (1964).

As aldosterone antagonists, the compounds of formulae I and II are useful in the treatment of primary aldosteronism and as diuretic agents especially in treatment of hepatic cirrhosis and in nephrotic syndrome; also are useful in treating various types of hypertension and in congestive heart failure. The aldosterone antagonists are usually administered orally in effective doses dependent upon the nature and severity of the ailment and on the age and weight of the patient.

In addition to the foregoing, the compounds of formulae I and II also exhibit anti-androgen and anabolic activity.

In addition to exhibiting aldosterone antagonist activity per se, the 3-oxo-4-androstene-17-spirobutanones of formulae I and II are also useful as intermediates since, upon treatment with a Baeyer-Villager oxidation reagent, e.g. with alkaline hydrogen peroxide, the 3-oxo-4-androstene-17-spirobutanones are converted to the corresponding 3-oxo-17α-4-pregnene-21,17β-carbolactones which are known, anti-aldosterone agents.

Of the 3-oxo-4-androstene-17-spirobutanones of above formulae I and II, preferred compounds include (17R)-spiro-[4-androstene-17,1'-cyclobutane]-3,2'-dione, and the 6-dehydro and 19-nor analogs thereof since each, in addition to possessing anti-aldosterone activity per se, upon treatment with alkaline hydrogen peroxide, are converted respectively to 3-oxo-17α-4-pregnene-21,17β-carbolactone, the 6-dehydro analog thereof (also known as ALDADIENE), and the 19-nor analogs thereof, all of which are known compounds useful as aldosterone antagonists.

Another composition-of-matter aspect of this invention is directed to steroidal 17-cyclobutanones valuable mainly as intermediates and includes compounds selected from the group consisting of a 3-hydroxy-5ξ-androstane-17-spirocyclobutanone of the following formula III:

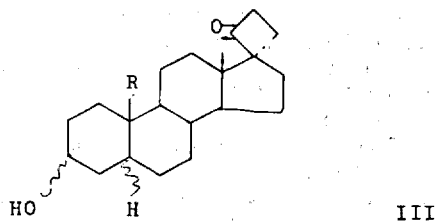

wherein R is a member selected from the group consisting of hydrogen and methyl;
  the 5-dehydro analogs thereof when R is methyl;
  the 3-lower alkoxy-3,5-bis-dehydro derivatives thereof;
  the 3-lower alkoxy-7α-acetylthio-3,5-bis-dehydro derivatives thereof;
  the 3-lower alkoxy-9α-fluoro-11β-hydroxy-3,5-bis-dehydro derivatives thereof when R is methyl;
  the 3-lower alkoxy-7α-acetylthio-9α-fluoro-11β-hydroxy-3,5-bis-dehydro derivatives thereof when R is methyl; and
  the 5(10)-dehydro analog thereof and the 3-lower alkoxy-2,5(10)-bis-dehydro derivatives thereof when R is hydrogen.

In the specification and claims, by "lower alkoxy" are contemplated straight chain, branched and cyclic alkyloxy groups having up to six carbon atoms, including methoxy, ethoxy, isopropoxy, and cyclopentyloxy.

Typical androstane-17-spirocyclobutanone intermediates of this invention thus include steroids of formula III such as:
  (17R)-spiro-[3β-hydroxy-5α-androstane-17,1'-cyclobutan]-2'-one, the 5β-epimer thereof and the 3α-hydroxy-5α- and 3α-hydroxy-5β-isomers thereof (compounds of formula III wherein R is methyl) as well as the 19-nor analogs of the foregoing (compounds of formula III wherein R is hydrogen);
  (17R)-spiro-[3β-hydroxy-5-androstene-17,1'-cyclobutan]-2'-one and the 3α-epimer thereof (5-dehydro compounds of formula III when R is methyl);
  (17R)-spiro-[3-ethoxy-3,5-androstadiene-17,1'-cyclobutan]-2'-one, the 19-nor analogs thereof and the 7α-acetylthio derivatives of the foregoing (3-ethoxy-3,5-bis-dehydro compounds of formula III and 7α-acetylthio derivatives thereof);
  (17R)-spiro-[3-ethoxy-9α-fluoro-11β-hydroxy-3,5-androstadiene-17,1'-cyclobutan]-2'-one and the 7α-acetylthio derivatives thereof (3-ethoxy-9α-fluoro-11β-hydroxy-3,5-bis-dehydro derivative of formula III and the 7α-acetylthio derivative thereof);
  (17R)-spiro-[3β-hydroxy-19-nor-5(10)-androstene-17,1'-cyclobutan]-2'-one (5(10)-dehydro analog of formula III when R is hydrogen); and
  (17R)-spiro-[3-methoxy-2,5(10)-androstadiene-17,1'-cyclobutan]-2'-one (2,5(10)-bis-dehydro analog of formula III when R is hydrogen).

The foregoing compounds of formula III are useful as intermediates as discussed hereinbelow and specifically described in the examples. Particularly useful compounds are the above-listed (17R)-spiro-[3-alkoxy-3,5-androstadiene-17,1'-cyclobutan]-2'-ones which, in addition to being useful as intermediates in the preparation of the corresponding 3-oxo-4-androstene-17-spirocyclobutanones having anti-aldosterone activity, are also useful per se as aldosterone antagonists.

The androstane-(17R)-spirocyclobutanones of this invention as defined by formulae I, II and III are white crystalline solids and are soluble in chloroform, methylene chloride, acetone and ethyl acetate and insoluble in water and hexane.

PROCESS ASPECTS OF THE INVENTION

The process of this invention whereby a 17-oxo-androstane is converted to a (17R)-spiro-[androstane-17,1'-cyclobutan]-2'-one of this invention is defined as the process for the preparation of a compound selected from the group consisting of 3-hydroxy-androstane-17-spirocyclobutanone of following formula III;

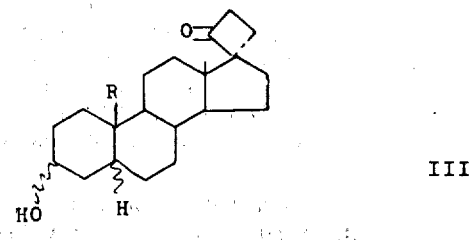

wherein R is a member selected from the group consisting of hydrogen and methyl;
  the 5-dehydro analogs thereof when R is methyl;
  the 3-lower alkoxy-3,5-bis-dehydro derivatives thereof;
  the 3-lower alkoxy-9α-fluoro-11β-hydroxy-3,5-bis-dehydro derivatives thereof when R is methyl; and
  the 5(10)-dehydro analog thereof and the 3-lower alkoxy-2,5(10)-bis-dehydro derivatives thereof when R is hydrogen,
which comprises the reaction of a compound selected from the group consisting of a 17-oxo androstane of following formula A;

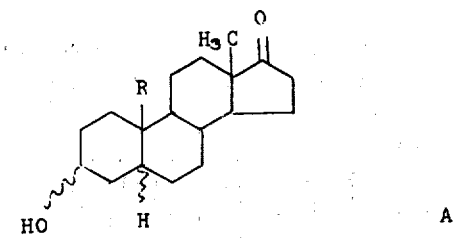

wherein R is a member selected from the group consisting of hydrogen and methyl;

the 5-dehydro analogs thereof when R is methyl;
the 3-lower alkoxy-3,5-bis-dehydro derivatives thereof;
the 3-lower alkoxy-9α-fluoro-11β-hydroxy-3,5-bis-dehydro derivatives thereof when R is methyl; and
the 5(10)-dehydro analog thereof and the 3-lower alkoxy-2,5(10)-bis-dehydro derivatives thereof when R is hydrogen,
with a reagent containing an arylsulfurcyclopropane grouping selected from the group consisting of a cyclopropylarylsulfide and a cyclopropylarylsulfonium salt having a non-nucleophilic anion in a non-reactive organic solvent together with a strong base;
followed by treatment in situ of the intermediate thereby formed with a member selected from the group consisting of an aqueous acid and, when said reagent is a cyclopropylarylsulfonium salt, with water.

In carrying out the process of this invention, a 17-oxo androstane having all other oxo functions protected is first reacted with a reagent containing an arylsulfurcyclopropane grouping together with a strong base in a non-reactive organic solvent, the intermediate thereby formed is then reacted in situ with an aqueous acid or, when the reagent is a cyclopropylarylsulfonium salt, reaction with water alone is sufficient, and the resulting (17R)-spiro-[androstane-17,1'-cyclobutan]-2'-one is isolated utilizing known techniques.

Reagents containing an arylsulfurcyclopropane grouping useful in our process include cyclopropylarylsulfides, such as cyclopropylphenylsulfide, and cyclopropylarylsulfonium salts having a non-nucleophilic anion, such as N,N-dimethylaminocyclopropylphenyloxosulfonium tetrafluoroborate (also known as "fluoroborate") and diphenylcyclopropylsulfonium tetrafluoroborate (also called "fluoroborate").

In this process, preferred as reagents are the cyclopropylarylsulfonium salts with fluoroborate (i.e. tetrafluoroborate) being the preferred non-nucleophilic anion therein; however, any non-nucleophilic anion, e.g. perchlorate, is useful in our process.

Although certain strong bases work best with each of the arylsulfurcyclopropane reagents such as discussed hereinbelow, any strong base may be used which is sufficiently strong to abstract a hydrogen from the tertiary carbon in the cyclopropane ring in the arylsulfurcyclopropane reagent.

"Non-reactive organic solvents" suitable for use in our process are organic solvents in which the starting 17-oxo steroid and the reagent/strong base mixture are at least partially soluble and which will not react with the reagent so that competing side reactions are minimized. Suitable organic solvents for this process include cyclic ethers such as dioxane and preferably tetrahydrofuran, dimethylsulfoxide, 1,2-dimethoxyethane (glyme), bis(2-methoxyethyl)ether (diglyme) and lower alkanols when an alkali metal alcoholate is used as strong base in the process. When a cyclopropylarylsulfide (e.g. cyclopropylphenylsulfide) is used as reagent together with an alkyl lithium or aryl lithium as base (e.g. butyl lithium) the solvent of choice is tetrahydrofuran; whereas when a cyclopropylarylsulfonium salt together with a base is used as reagent (e.g. N,N-dimethylaminocyclopropylphenyloxosulfonium fluoroborate or diphenylcyclopropylsulfonium fluoroborate, the solvent of choice is usually dimethylsulfoxide.

In our process, reagent/strong base/non-reactive solvent combinations which are most useful include cyclopropylarylsulfides such as cyclopropylphenylsulfide, together with an aryl lithium or alkyl lithium base, preferably butyl lithium, in an alicyclic ether, preferably tetrahydrofuran. Other preferred combinations are those utilizing cyclopropylarylsulfonium salts having a non-nucleophilic anion as reagent, of which preferred are N,N-dimethylaminocyclopropylphenyloxosulfonium salts and diphenylcyclopropylsulfonium salts, both preferably having tetrafluoroborate as the non-nucleophilic anion. N,N-dimethylaminocyclopropylphenyloxosulfonium tetrafluoroborate is usually used together with sodium hydride as the strong base in dimethylsulfoxide as non-reactive solvent, while diphenylcyclopropylsulfonium tetrafluoroborate is conveniently used together with dimsyl sodium (i.e. dimethylsulfoxide sodium salt) as strong base in glyme as non-reactive solvent, or together with potassium tert.-butoxide as strong base in tert.-butanol as non-reactive solvent, or, preferably, together with potassium hydroxide as strong base in dimethylsulfoxide as the non-reactive solvent.

After reaction of a 17-oxo androstane with a reagent containing an arylsulfurcyclopropane grouping together with a base in a non-reactive solvent, the intermediate thereby formed is then reacted in situ with dilute aqueous acid or, when the reagent is a cyclopropylarylsulfonium salt, the reaction may be with water alone, and there is formed a (17R)-spiro-[androstane-17,1'-cyclobutan]-2'-one which is isolated utilizing conventional techniques.

In this step of our process, any aqueous acid (e.g. hydrochloric, sulfuric, phosphoric, acetic, benzoic) may be used. A preferred aqueous acid for this process is fluoroboric acid.

Our process is preferably carried out at room temperature or at lower temperatures in the absence of oxygen; and usually is carried out under an atmosphere of an inert gas (e.g. argon or nitrogen).

The requisite 17-oxo androstane starting compounds of our process are well known in the art and preferably devoid of other oxo functions to prevent competing side reactions. When other oxo functions are present in a 17-oxo starting steroid, prior to reaction with a reagent containing an arylsulfurcyclopropane grouping together with a strong base and a non-reactive organic salt according to our process, the other oxo functions are protected by conversion thereof to functional derivatives by methods known in the art. Thus, for example, 9α-fluoro-11β-hydroxy-4-androstene-3,17-dione is converted to the enol ether derivative thereof by treatment iwth triethylorthoformate and sulfuric acid in dioxane, and the resulting 3-ethoxy-9α-fluoro-11β-hydroxy-3,5-androstadiene-17-one, upon reaction with cyclopropylsulfonium tetrafluoroborate and dimsyl sodium in 1,2-dimethoxyethane at −40° C followed by treatment of the intermediate thereby formed with aqueous fluoroboric acid according to our process, is converted to the corresponding (17R)-spiro-[17,1'-cyclobutan]-2'-one of my invention, i.e. (17R)-spiro-[3-ethoxy-9α-fluoro-11β-hydroxy-3,5-androstadiene-17,1'-cyclobutan]-2'-one which, upon hydrolysis with dilute hydrochloric acid in acetone, yields a 3-oxo-4-dehydro-(17R)-spirocyclobutanone of our invention, i.e. (17R)-spiro-[9α-fluoro-11β-hydroxy-4-androstene-17,1'-cyclobutane]-3,2'-dione.

Similarly, when preparing a (17R)-spiro-[19-norandrostane-17,1'-cyclobutane]-3,2'-dione of our invention, the requisite intermediates are either a 3-alkoxy (e.g. 3-methoxy)-19-nor-2,5(10)-androstandiene-17-one or 3β-hydroxy-19-nor-5(10)-androstene-17-one. Each of the foregoing intermediates, upon reaction with cyclopropyldiphenylsulfonium fluoroborate and potassium hydroxide in dimethylsulfoxide followed by reaction in situ of the resulting intermediate with an acid such as aqueous fluoroboric acid or with aqueous acetic acid according to our process, yields each of the corresponding (17R)-spirocyclobutanones, i.e. (17R)-spiro-[3-methoxy-19-nor-2,5(10)-androstadiene-17,1'-cyclobutan]-2'-one and (17R)-spiro-[3β-hydroxy-19-nor-5(10)-androstene-17,1'-cyclobutan]-2'-one, respectively. Acid hydrolysis of the 3-alkoxy-19-nor-2,5(10)-androstadiene cyclobutanone of our invention (such as with hydrochloric acid in acetone), or treatment of the 3-hydroxy-5(10)-androstene cyclobutanone with an oxidizing agent (e.g. aluminum tri-tertiary butoxide in acetone/benzene) yields a 3-oxo-4-dehydro-19-nor-androstane-17-cyclobutanone of this invention, i.e. (17R)-spiro-[19-nor-4-androstene-17,1'-cyclobutane]-3,2'-dione.

When carrying out the process of this invention, we prefer to utilize cyclopropylidiphenylsulfonium fluoroborate as reagent in dimethylsulfoxide as inert organic solvent and with powdered potassium hydroxide as the strong base. Usually, to a 17-oxo androstane devoid of other oxo functions (e.g. 3β-hydroxy-5-androstane-17-one) in an inert organic solvent (e.g. dimethylsulfoxide) there is added from about 1 to about 5 equivalents of the reagent containing an arylsulfurcyclopropane grouping (e.g. cyclopropyldiphenylsulfonium fluoroborate) and the reaction mixture is stirred under an inert atmosphere (e.g. under nitrogen) at room temperature for a few minutes. About 3 to 25 equivalents of powdered potassium hydroxide is then added, the reaction mixture stirred under an inert atmosphere for a few hours, then is poured into a large volume of ice water, and acetic or fluoroboric acid is added until the pH of the reaction mixture is at about pH 7 (i.e. treatment of the intermediate in situ with aqueous acid). The resulting (17R)-spiro-[androstane-17,1'-cyclobutan]-2'-one product (e.g. (17R)-spiro-[3β-hydroxy-5-androstene-17,1'-cyclobutan]-2'-one) is then isolated and purified utilizing techniques well known in the art; for example, by extraction with ethyl acetate, washing the combined organic solution with water, evaporation of the organic solution in vacuo to a residue followed by chromatography thereof.

The process of this invention whereby a 17-oxo androstane devoid of other oxo functions upon treatment with a cyclopropylarylsulfonium salt and strong base in an organic solvent is converted to a (17R)-spiro-[androstane-17,1'-cyclobutan]-2'-one is most conveniently carried out on 3-hydroxyandrostane-17-ones, 3-hydroxy-5-androstene-17-ones, on 4-androstene-3,17-diones, on 3β-hydroxy-19-nor-5(10)-androstene-17-ones or on 3-alkoxy-19-nor-2,5(10)-androstadiene-17-ones wherein any 3-oxo function is protected by conversion to functional derivatives thereof as discussed hereinabove, whereby are prepared (17R)-spiro-[3-hydroxy-androstane-17,1'-cyclobutan]-2'-ones,
(17R)-spiro-[3-hydroxy-5-androstene-17,1'-cyclobutan]-2'-ones,
(17R)-spiro-[4-androstene-17,1'-cyclobutane]-3,2'-dione, and 3-alkoxy-3,5-bis-dehydro enol ethers thereof,
(17R)-spiro-[3β-hydroxy-19-nor-5(10)-androstene-17,1'-cyclobutan]-2'-one,
(17R)-spiro-[3-alkoxy-19-nor-2,5(10)-androstadiene-17,1'-cyclobutan]-2'-one, respectively.

From the foregoing derivatives the 1,4-bis-dehydro-, 4,6-bis-dehydro and 1,4,6-tris-dehydro derivative of this invention are prepared utilizing known techniques. Thus, 3-oxo-4,6-androstadiene-17-cyclobutanones or 3-oxo-19-nor-4,6-androstadiene-17-cyclobutanones of our invention are prepared from the corresponding 3-oxo-4-androstene-17-cyclobutanones or 19-nor analogs thereof by treatment thereof with dichlorodicyanobenzoquinone (DDQ) and anhydrous hydrogen chloride in dioxane. Alternatively, reaction of an enol ether of a 3-oxo-4-androstene-17-cyclobutanone (i.e. a 3-alkoxy-3,5-androstadiene-17-cyclobutanone) with DDQ under neutral conditions in aqueous acetone also produces a 3-oxo-4,6-androstadiene-17-cyclobutanone of this invention.

Thus, (17R)-spiro-[4,6-androstadiene-17,1'-cyclobutane]-3,2'-dione is prepared by the reaction of (17R)-spiro-[4-androstene-17,1'-cyclobutane]-3,2'-dione with DDQ and hydrogen chloride in dioxane or by the reaction of (17R)-spiro-[3-ethoxy-3,5-androstadiene-17,1'-cyclobutane]-3,2'-dione with DDQ in aqueous acetone.

The 3-oxo-1,4-androstadiene-17-cyclobutanones (e.g. (17R)-spiro-[1,4-androstadiene-17,1'-cyclobutane]-3,2'-dione) and 3-oxo-1,4,6-androstatriene-17-cyclobutanones (e.g. (17R)-spiro-[1,4,6-androstatriene-17,1'-cyclobutane]-3,2'-dione) are conveniently prepared from the corresponding 4-dehydro and 4,6-bis-dehydro analogs (e.g. (17R)-spiro-[3-oxo-4-androstene-17,1'-cyclobutane]-3,2'-dione and the 6-dehydro analog thereof) by treatment with DDQ under neutral conditions at elevated temperatures.

The 7α-thioacetyl derivatives of formula I are derived from the corresponding 7-unsubstituted-6-dehydro analog by treatment thereof with thioacetic acid at elevated temperatures. The 7α-thioacetyl-4-androstene-3-one derivative of formula I thereby formed is then conveniently converted to a 3-alkoxy-3,5-androstadiene cyclobutanone derivative of formula III by reaction with a trialkylorthoformate and sulfuric acid in dioxane. Thus, (17R)-spiro-[4,6-androstadiene-17,1'-cyclobutane]-3,2'-dione, upon treatment with thioacetic acid at 100°C yields (17R)-spiro-]7α-thioacetyl-4-androstene-17,1'-cyclobutane]-3,2'-dione of formula I, which, upon treatment with triethylorthoformate and sulfuric acid yields (17R)-spiro-[3-ethoxy-7α-thioacetyl-3,5-androstadiene-17,1'-cyclobutane]-3,2'-dione, a 3-alkoxy-3,5-bis-dehydro analog of formula III.

The 6β,7β-cyclomethylene cyclobutanone of formula II is conveniently prepared from (17R)-spiro-[3β-hydroxy-5-androstene-17,1'-cyclobutan]-2'-one by treatment thereof with aluminum tertiary butoxide in acetone after protection of the 2'-oxo group by conversion thereof to a ketal (e.g. to the 2',2'-ethylenedioxy derivative), followed by treatment of the 3-oxo-4-dehydro derivative thereby formed (e.g. (17R)-spiro-[2',2'- ethylenedioxy-4-androstene-17,1'-cyclobutan]-3-one with chloranil at elevated temperatures and thence treatment of the resulting 6-dehydro analog (i.e. (17R)-spiro-[2',2'-ethylenedioxy-4,6-androstadiene-17,1'-cyclobutan]-3-one with dimethyloxosulfonium-methylide in dimethylsulfoxide whereby is formed (17R)-spiro-[2,40 ,2'-ethylenedioxy-6β,7β-cyclomethylene-4-androstene-17,1'-cyclobutan]-3-one. Removal of the ketal function with p-toluenensulfonic acid in acetone yields the compound of formula II, i.e. (17R)-spiro-[6β,7β-cyclomethylene-4-androstene-17,1'-cyclobutane]-3,2'-dione. Treatment of the foregoing with DDQ in refluxing benzene/dioxane yields the corresponding 1-dehydro analog (17R)-spiro-[6β,7β-cyclomethylene-1,4-androstadiene-17,1'-cyclobutane]-3,2'-dione.

All the compounds of our invention as defined by formulae I (wherein W is hydrogen), II and III; upon treatment with a Baeyer-Villager oxidation reagent, preferably alkaline hydrogen peroxide, are converted to the corresponding carbolactones of following formulae IV and V:

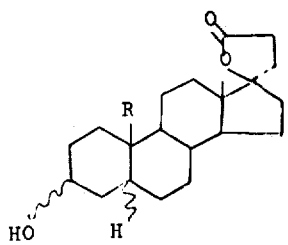

IV and

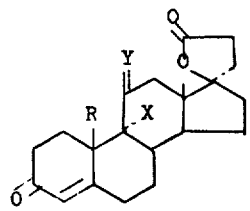

V wherein R is a member selected from the group consisting of hydrogen and methyl;

X and Y are both hydrogen, or X is fluorine and Y is (H,βOH) provided R is methyl;

the 5-dehydro analogs of the compounds of formula IV when R is methyl;

the 3-lower alkoxy-3,5-bis-dehydro derivatives of formula IV;

the 5(10)-dehydro analog thereof and the 3-lower alkoxy-2,5(10)-bis-dehydro derivatives of formula IV provided R is hydrogen;

the 6-dehydro analogs of formula V;

the 1-dehydro and 1,6-bis-dehydro analogs of formula V when R is methyl;

the 6β,7β-cyclomethylene derivatives of formula V when R is methyl and X and Y are hydrogen, and the 1-dehydro analog thereof.

Baeyer-Villager oxidation methods are well known in the art and are described, for example, by C. H. Hassall in *Organic Reactions*, Vol. 9, pages 73–106 (1957). Baeyer-Villager oxidation reagents useful in converting a cyclobutanone of our invention (i.e. a compound of formulae I, II and III) to a spirolactone of formulae IV and V include peracids such as peracetic acid, trifluoroacetic acid, and perbenzoic acid, hydrogen peroxide in inert organic solvents (e.g. ether, pyridine, dioxane, etc.), hypohalous acids such as hypochlorous acid, alkali metal hypohalites such as sodium hypobromite, and, preferably, alkaline hydrogen peroxide.

The compounds of formula V are known compounds useful as aldosterone antagonists. The compounds of formula IV are known compounds useful as intermediates in preparing the 19-nor compounds of formula V and the 3-oxo-6-dehydro analogs of formula V. Thus, any of the 3-hydroxy-5(ξ)-17α-pregnane-21,17β-carbolactones of formula IV wherein R is methyl, upon treatment with chromic acid in acetone yields 3-oxo-5(ξ)-17α-pregnane-21,17β-carbolactone which, upon treatment with bromine in dioxane yields a 2,4-dibromo-3-oxo-5(ξ)-17α-pregnane-21,17β-carbolactone which, upon treatment with lithium bromide in dimethyl acetamide using known techniques, yields 3-oxo-17α-4,6-pregnadiene-21,17β-carbolactone (a 6-dehydro compound of formula V wherein R is methyl, X and Y are hydrogen), an antialdosterone agent also known as Aldadiene.

Alternatively, any of the 3-hydroxy-5(ξ)-19-nor-17α-pregnane-21,17β-carbolactones of formula IV, upon treatment with chromic acid, yields 3-oxo-5(ξ)-17α-19-nor-pregnane-21,17β-carbolactone which, upon treatment with DDQ under neutral conditions in benzene, yields the corresponding 4-dehydro compound, i.e. 3-oxo-17α-4-pregnene-21,17β-carbolactone, an anti-aldosterone agent.

The processes described hereinabove are illustrated in detail in the Examples hereinbelow and should not be construed as limiting the scope of our invention, equivalents thereof and products produced thereby, which will be obvious to one skilled in the art, being considered a part of the invention.

EXAMPLE 1

(17R)-SPIRO-[3-HYDROXY-5-ANDROSTENE-17,1'-CYCLOBUTAN]-2'-ONES

A.

(17R)-Spiro-[3β-Hydroxy-5-Androstene-17,1'-Cyclobutan]-2'-One

Dissolve 500 mg. of 3β-hydroxy-5-androstene-17-one and 2.7 gms. of cyclopropyldiphenylsulfonium fluoroborate (5 equivalents) in 10 ml of dimethylsulfoxide. Stir at room temperature under an atmosphere of nitrogen and add 2.19 gms. of powdered potassium hydroxide (25 equivalents) in one portion and continue stirring for two hours. Pour the reaction mixture over 300 ml. of ice water and add glacial acetic acid until the solution is at about pH 7. Extract the solution with three 150 ml. portions of ethyl acetate, wash the combined ethyl acetate extracts with three 100 ml. portions of water, then dry the ethyl acetate over anhydrous magnesium sulfate and evaporate the solution in vacuo to a residue comprising (17R)-spiro-[3β-hydroxy-5-androstene-17,1'-cyclobutan]-2'-one. Purify by chromatographing over 50 gms. of silica gel eluting with ether/hexane (1:1). Combine the like fractions containing the (17R)-spiro compound as determined by thin layer chromatography and evaporate in vacuo to a residue of (17R)-spiro-[ 3β-hydroxy-5-androstene-17,1'-cyclobutan]-2'-one; yield 230 mg. (40%); m.p. 174°-178°C; [M]⁺ 328; $\gamma_{cm}^{-1}$ (nujol) 5.70 mμ; NMR (Dimethylsulfoxide-d₆); δ 0.77 ($C_{13}$–$CH_3$); 0.93 ($C_{10}$–$CH_3$); 4.56 (3α-H; mult.); 5.29 ($C_6$-H; mult.).

B. In a manner similar to that described in Example 1-A, treat 3α-hydroxy-5-androstene-17-one with cyclopropyldiphenylsulfonium fluoroborate and potassium hydroxide in dimethylsulfoxide, and isolate and purify the resultant product to obtain (17R)-spiro-[3α-hydroxy-5-androstene-17,1'-cyclobutan]-2'-one.

C. To cyclopropylphenylsulfide (2 gms.) in 20 ml. of dry tetrahydrofuran under an atmosphere of nitrogen add n-butyl lithium (0.64 ml. of 1.6 molar solution in hexane). Stir under an atmosphere of nitrogen at 0°C for 2 hours, then add dropwise a solution of 3β-hydroxy-5-androstene-17-one (2 gms.) in 10 ml. of dry tetrahydrofuran. Continue stirring under an atmosphere of nitrogen at 0°C for 30 minutes, then cautiously add 5 ml. of 1 molar aqueous fluoroboric acid. Continue stirring for an additional 30 minutes, then add chloroform, wash the organic solution 3 times with water, dry over anhydrous magnesium sulfate and evaporate in vacuo to a residue comprising (17R)-spiro-[3β-hydroxy-5α-androstene-17,1'-cyclobutan]-2'-one.

D. To N,N-dimethylaminocyclopropylphenyloxosulfonium fluoroborate (1 gm., 3.37 mmoles) in dry dimethylsulfoxide (5 ml.) under an atmosphere of nitrogen add sodium hydride (0.0789 gms., 3.2 mmoles) keeping the reaction mixture at room temperature by means of external cooling. Stir the reaction mixture for ½ hour at room temperature, then add dropwise a solution of 3β-hydroxy-5-androstene-17-one (0.92 gms., 3.2 mmoles) in dimethylsulfoxide (5 ml.). Continue stirring the reaction mixture under an atmosphere of nitrogen at room temperature for 24 hours, then add water. Extract the reaction mixture with ethyl acetate and wash the combined organic extracts with water, dry over anhydrous magnesium sulfate and evaporate an vacuo to a residue comprising (17R)-spiro-[3β-hydroxy-5-androstene-17,1'-cyclobutan]-2'-one.

EXAMPLE II (17R)-SPIRO-[3-HYDROXYANDROSTANE-17,1'-CYCLOBUTAN]-2'-ONES

A.

(17R)-Spiro-[3β-hydroxy-5α-androstane-17,1'-cyclobutan]-2'-one

Dissolve 250 mg. of 3β-hydroxy-5α-androstane-17-one and 1.35 gm. of cyclopropyldiphenylsulfonium fluoroborate in 5 ml. of dimethylsulfoxide. Stir at room temperature under an atmosphere of nitrogen, then add 1.098 gm. of powdered potassium hydroxide and stir for two hours. Pour the reaction mixture over ice water and add glacial acetic acid until the solution is at about pH 7. Extract the aqueous solution with ethyl acetate, then wash the combined organic extracts with water, then dry over magnesium sulfate and evaporate in vacuo to a residue comprising (17R)-spiro-[3β-hydroxy-5α-androstane-17,1'-cyclobutan]-2'-one. Purify by chromatographing on silica gel (25 gm.) eluting with ether:hexane (1:1). Combine the like fractions containing the (17R)-spiro product as determined by thin layer chromatography and evaporate in vacuo to a residue of (17R)-spiro-[3β-hydroxy-5α-androstane-17,1'-cyclobutan]-2'-one; yield 144 mg. (55% theory); m.p. 175°–180°C, $[\alpha]_D^{26}$ + 49.3° (chloroform); $[M]^+$ 330, $\gamma_{cm}^{-1}$ (nujol); 5.66 mμ; NMR (dimethylsulfoxide-$d_6$); 80.74 ($C_{13}$ and $C_{10}$-$CH_3$).

B. In a manner similar to that described in Example II-A treat each of the following with cyclopropyldiphenylsulfonium fluoroborate and potassium hydroxide in dimethylsulfoxide.

1. 3β-hydroxy-5β-androstane-17-one,
2. 3α-hydroxy-5α-androstane-17-one,
3. 3α-hydroxy-5β-androstane-17-one,
4. 3β-hydroxy-19-nor-5α-androstane-17-one,
5. 3β-hydroxy-19-nor-5β-androstane-17-one,
6. 3α-hydroxy-19-nor-5α-androstane-17-one,
7. 3α-hydroxy-19-nor-5β-androstane-17-one.

Isolate and purify each of the resultant products in a manner similar to that described in Example II-A to obtain, respectively, 1. (17R)-spiro-[3β-hydroxy-5β-androstane-17,1'-cyclobutan]-2'-one,
2. (17R)-spiro-[3α-hydroxy-5α-androstane-17,1'-cyclobutan]-2'-one,
3. (17R)-spiro-[3α-hydroxy-5β-androstane-17,1'-cyclobutan]-2'-one,
4. (17R)-spiro-[3β-hydroxy-19-nor-5α-androstane-17,1'-cyclobutan]-2'-one,
5. (17R)-spiro-[3β-hydroxy-19-nor-5β-androstane-17,1'-cyclobutan]-2'-one,
6. (17R)-spiro-[3α-hydroxy-19-nor-5α-androstane-17,1'-cyclobutan]-2'-one,
7. (17R)-spiro-[3α-hydroxy-19-nor-5β-androstane-17,1'-cyclobutan]-2'-one.

EXAMPLE III (17R)-SPIRO-[3-ETHOXY-3,5-ANDROSTADIENE-17,1'-CYCLOBUTAN]-2'-ONE

To 3.2 gm. of 3-ethoxy-3,5-androstadiene-17-one in 77.5 ml. of dry dimethylsulfoxide add 6.4 gm. (2 equivalents) of cyclopropyldiphenylsulfonium fluoroborate and 5.75 gm. (10 equivalents) of potassium hydroxide. Stir the reaction mixture at room temperature under an atmosphere of nitrogen for 3.5 hours. Pour into water, bring the aqueous solution to about pH 7 with glacial acetic acid, then extract the reaction mixture with three 200 ml. portions of ethyl acetate. Wash the combined ethyl acetate extract with three portions of water, dry over anhydrous magnesium sulfate and evaporate at room temperature in vacuo to a residue comprising (17R)-spiro-[3-ethoxy-3,5-androstadiene-17,1'-cyclobutan]-2'-one, which is used without further purification in the procedure described in Example VI-A.

EXAMPLE IV (17R)-SPIRO-[3-METHOXY-19-NOR-2,5(10)-ANDROSTADIENE-17,1'-CYCLOBUTAN]-2'-ONE

In a manner similar to that described in Example III treat 3-methoxy-19-nor-2,5(10)-androstadiene-17-one with cyclopropyldiphenylsulfonium fluoroborate and potassium hydroxide in dimethylsulfoxide. Isolate the resultant product in a manner similar to that described in Example III to obtain (17R)-spiro-[3-methoxy-19-nor-2,5(10)-androstadiene-17,1'-cyclobutan]-2'-one, which is used without further purification in the procedure described in Example VII-A.

EXAMPLE V (17R)-SPIRO-[3β-HYDROXY-19-NOR-5(10)-ANDROSTENE-17,1'-CYCLOBUTAN]-2'-ONE

In a manner similar to that described in Example I-A treat 3β-hydroxy-19-nor-5(10)-androstene-17-one in dimethylsulfoxide with cyclopropyldiphenylsulfonium fluoroborate and potassium hydroxide. Isolate the resultant product in a manner similar to that described in Example I-A to obtain (17R)-spiro-[3β-hydroxy-19- nor-5(10)-androstene-17,1'-cyclobutan]-2'-one, which is used without further purification in the procedure described in Example VII-B.

EXAMPLE VI

(17R)-SPIRO-[4-ANDROSTENE-17,1'-CYCLOBUTANE]-3,2'-DIONE

A. Dissolve the total product of (17R)-spiro-[3-ethoxy-3,5-androstadiene-17,1'-cyclobutan]-2'-one obtained in Example III in 150 ml. of acetone containing 18 ml. of 1 N aqueous hydrochloric acid. Allow the reaction mixture to stand at room temperature for 30 minutes, then add pyridine until the solution is at about pH 7, then evaporate in vacuo at room temperature to a residue. Dissolve the residue in 500 ml. of ethyl acetate, wash the ethyl acetate solution with three portions of water, then dry over magnesium sulfate and evaporate in vacuo to a residue comprising (17R)-spiro-[4-androstene-17,1'-cyclobutane]-3,2'-dione. Purify by chromatography on 300 gm. of silica gel eluting with chloroform:methylene chloride:ethyl acetate (50:50:1). Combine the like fractions as determined by thin layer chromatography, then evaporate the combined eluates in vacuo to a residue of (17R)-spiro-[4-androstene-17,1'-cyclobutane]-3,2'-dione; yield 1.23 gm. (37%); m.p. 188°–192°C; $[\alpha]_D^{26} + 147.7°$ (dimethylformamide); $\gamma_{cm}^{-1}$, (nujol); 5.68 m$\mu$; $\lambda_{max}^{methanol}$ 241 nm $\epsilon$ 15,700; NMR (dimethylsulfoxide-$d_6$); $\delta$ 0.82 ($C_{13}$-$CH_3$); 1.16 ($C_{10}$-$CH_3$).

Alternatively, the compound of this example is prepared as follows.

B. To 100 mg. of (17R)-spiro-[3$\beta$-hydroxy-5-androstene-17,1'-cyclobutan]-2'-one in 3.75 ml. of ethyl acetate and 7.5 ml. of dry benzene add 97 mg. of aluminum tri-tertiary butoxide. Heat the reaction mixture at reflux temperature for 24 hours, then add an additional 97 mg. of aluminum tri-tertiary butoxide and reflux for an additional 24 hours. Repeat this procedure once again, then pour the reaction mixture into 300 ml. of water containing 1 N hydrochloric acid. Extract the aqueous mixture with three portions of 100 ml. of ethyl acetate, wash the combined ethyl acetate extracts with three 100 ml. portions of water, then dry over anhydrous magnesium sulfate and evaporate to a residue comprising (17R)-spiro-[4-androstene-17,1'-cyclobutane]-3,2'-dione. Purify by crystallization from acetone-hexane to obtain 88 mg. (88%) of (17R)-spiro-[4-androstene-17,1'-cyclobutane]-3,2'-dione having physical constants identical to those set forth in Example VI-A.

EXAMPLE VII

(17R)-SPIRO-[19-NOR-4-ANDROSTENE-17,1'-CYCLOBUTANE]-3,2'-DIONE

A. In a manner similar to that described in Example VI-A treat (17R)-spiro-[3-methoxy-19-nor-2,5-(10)-androstadiene-17,1'-cyclobutan]-2'-one with hydrochloric acid in acetone. Isolate and purify the resultant product in a manner similar to that described in Example VI-A to obtain (17R)-spiro-[19-nor-4-androstene-17,1'-cyclobutane]-3,2'-dione.

Alternatively, the compound of this example is prepared as follows:

B. In a manner similar to that described in Example VI-B treat (17R)-spiro-[3$\beta$-hydroxy-19-nor-5(10)-androstene-17,1'-cyclobutan]-2'-one with aluminum tri-tertiary butoxide with acetone in benzene. Isolate and purify the resultant product in a manner similar to that described in Example VI-B to obtain (17R)-spiro-[19-nor-4-androstene-17,1'-cyclobutane]-3,2'-dione.

EXAMPLE VIII

(17R)-SPIRO-[4,6-ANDROSTADIENE-17,1'-CYCLOBUTANE]-3,2'-DIONE AND THE 19-NOR ANALOG THEREOF

A. (17R)-spiro-[4,6-androstadiene-17,1'-cyclobutane[-3,2'-dione

To 0.8 gm. of (17R)-spiro-[4-androstene-17,1'-cyclobutane]-3,2'-dione in 48 ml. of dioxane containing 0.8 gm. of dry hydrogen chloride gas add 0.55 gm. (1 equivalent) of dichlorodicyanobenzoquinone (DDQ) and stir the reaction mixture at room temperature for 3.5 hours. Filter off the insolubles and evaporate the filtrate at room temperature in a draft oven. Dissolve the resultant residue in chlorform/ethyl acetate (1:1) and filter the solution through a column of neutral alumina (100 g.). Evaporate the filtrate and crystallize the resultant residue from acetone to obtain (17R)-spiro-[4,6-androstadiene-17,1'-cyclobutane]-3,2'-dione; yield 0.51 gm. (64% theory); m.p. 201°–204°C; $[\alpha]_D^{26} + 106.9°$ (dimethylformamide); $\lambda_{max}^{methanol}$ 285 nm ($\epsilon$26,380); [M]$^+$ 324; $\gamma_{cm}^{-1}$ (nujol); 5.68 (cyclobutanone), 6.01, 6,20, 6.32 m$\mu$; NMR (CDCl$_3$); $\delta$ 0.97 ($C_{13}$-$CH_3$; s), 1.13 ($C_{10}$-$CH_3$; s).

B. Alternatively, the compound of Example VIII-A is prepared as follows. Dissolve 40 mg. of (17R)-spiro-[3-ethoxy-3,5-androstadiene-17,1'-cyclobutan]-2'-one in 4 ml. of 95% aqueous acetone and add 26.8 mg. (1 equivalent) of re-crystallized DDQ in 0.8 ml. of 95% aqueous acetone. Stir at room temperature for three hours then evaporate in vacuo. Dissolve the resultant residue in chloroform/ethyl acetate (1:1) and filter through a short column of neutral alumina. Evaporate the filtrate to a residue of (17R)-spiro-[4,6-androstadiene-17,1'-cyclobutane]-3,2'-dione; yield 32 mg. (88% theory); $\lambda_{max}^{methanol}$ 283 nm ($\epsilon$ 23,000); infrared and nuclear magnetic resonance spectra are identical with those of the product of Example VIII-A.

C. In a manner similar to that described in Example VIII-A treat (17R)-spiro-[19-nor-4-androstene-17,1'-cyclobutane]-3,2'-dione with DDQ in dioxane containing hydrogen chloride gas. Isolate and purify the resultant product in a manner similar to that described hereinabove to obtain (17R)-spiro-[19-nor-4,6-androstadiene-17,1'-cyclobutane]-3,2'-dione.

EXAMPLE IX

3$\beta$-HYDROXY-17$\alpha$-5-PREGNENE-21,17$\beta$-CARBOLACTONE

A. Dissolve 20 mg. of (17R)-spiro-[3$\beta$-hydroxy-5-androstene-17,1'-cyclobutan]-2'-one in a mixture of 0.5 ml. of methanol, 0.0095 ml. of 30% hydrogen peroxide (2 equivalents) and 0.0133 ml. of 9 N aqueous sodium hydroxide (1 equivalent). Stir at room temperature under an atmosphere of nitrogen for 2 hours then adjust the solution to a pH of about 7 with 1 N hydrochloric acid, then evaporate the methanol in vacuo. Dissolve the resultant residue in ethyl acetate, wash the ethyl acetate solution with water then dry the ethyl acetate solution over anhydrous magnesium sulfate and evaporate in vacuo to a residue comprising 3$\beta$-hydroxy-17$\alpha$-5-pregnene-21,17$\beta$-carbolactone; yield 14 mg. (75% theory); m.p. 185°–189°C, mixed melting point with authentic 3β-hydroxy-17α-5-pregnene-21,17β-carbolactone, 185°-189°C; infrared spectrum is superimposable with that of the infrared spectrum of an authentic sample of 3β-hydroxy-17α-5-pregnene-21,17β-carbolactone.

B. In similar manner treat (17R)-spiro-[3α-hydroxy-5-androstene-17,1'-cyclobutan]-2'-one with alkaline hydrogen peroxide in aqueous methanol and isolate and purify the resultant product to obtain 3α-hydroxy-5-androstene-21,17β-carbolactone, which upon treatment with p-toluenesulfonyl chloride in pyridine followed by treatment of the resulting 3α-p-toluenesulfonate ester with potassium acetate in dimethylformamide yields 3β-acetoxy-17α-5-pregnene-21,17β-carbolactone. Hydrolysis of the foregoing with sodium bicarbonate in aqueous methanol yields 3β-hydroxy-17α-5-pregnene-21,17β-carbolactone.

EXAMPLE X

3-HYDROXY-17α,5α-PREGNANE-21,17β-CARBOLACTONES

A. 3β-hydroxy-17α,5α-pregnane-21,17β-carbolactone

Add 75 mg. of (17R)-spiro-]3β-hydroxy-5α-androstane-17,1'-cyclobutan]-2'-one in 1.9 ml. of methanol to a mixture of 0.036 ml. of 30% hydrogen peroxide and 0.05 ml. of 9 N sodium hydroxide and 1.9 ml. of methanol. Stir at room temperature under an atmosphere of nitrogen for 2 hours, then bring the solution to about pH 7 with 1 N hydrochloric acid. Concentrate the solution in vacuo, dissolve the resultant residue in ethyl acetate, wash the ethyl acetate solution with water, then dry over magnesium sulfate and evaporate in vacuo to a residue of 3β-hydroxy-17α,5α-pregnane-21,17β-carbolactone in quantitative yield; m.p. 193°-197°C when re-crystallized from acetone/hexane; $[\alpha]_D^{26}$ −28.1° (dimethylformamide); $[M]^+$ 346; $\gamma_{cm}^{-1}$ (nujol); 5.63 mμ; NMR (dimethylsulfoxide-d$_6$); δ 0.73 ($C_{10}$-CH$_3$), 1.13 ($C_{13}$-CH$_3$).

B. In similar manner treat each of
1. (17R)-spiro-[3β-hydroxy-5β-androstane-17,1'-cyclobutan]-2'-one,
2. (17R)-spiro-[3α-hydroxy-5α-androstane-17,1'-cyclobutan]-2'-one,
3. (17R)-spiro-[3α-hydroxy-5β-androstane-17,1'-cyclobutan]-2'-one,
4. (17R)-spiro-[3β-hydroxy-19-nor-5α-androstane-17,1'-cyclobutan]-2'-one,
5. (17R)-spiro-[3β-hydroxy-19-nor-5β-androstane-17,1'-cyclobutan]-2'-one,
6. (17R)-spiro-[3α-hydroxy-19-nor-5α-androstane-17,1'-cyclobutan]-2'-one,
7. (17R)-spiro-[3α-hydroxy-19-nor-5β-androstane-17,1'-cyclobutan]-2'-one, with alkaline hydrogen peroxide in methanol. Isolate and purify each of the resultant products in a manner similar to that described hereinabove to obtain, respectively,
1. 3β-hydroxy-17α,6β-pregnane-21,17β-carbolactone,
2. 3α-hydroxy-17α,5α-pregnane-21,17β-carbolactone,
3. 3α-hydroxy-17α,5β-pregnane-21,17β-carbolactone,
4. 3β-hydroxy-19-nor-17α,5α-pregnane-21,17β-carbolactone,
5. 3β-hydroxy-19-nor-17α,5β-pregnane-21,17β-carbolactone,
6. 3α-hydroxy-19-nor-17α,5α-pregnane-21,17β-carbolactone,
7. 3α-hydroxy-19-nor-17α,5β-pregnane-21,17β-carbolactone.

EXAMPLE XI

3-OXO-17α-4-PREGNENE-21,17β-CARBOLACTONE AND THE 19-NOR ANALOG THEREOF

A. To 0.0048 ml. of 30% hydrogen peroxide and 0.0068 ml. of 9 N sodium hydroxide in 0.5 ml. of methanol add 20 mg. of (17R)-spiro-[4-androstene-17,1'-cyclobutane]-3,2'-dione and stir the reaction mixture at room temperature under an atmosphere of nitrogen for 1 hour. Add water to the reaction mixture and add 1 N hydrochloric acid until the solution is at a pH of about 7. Extract the reaction mixture with ethyl acetate, wash the ethyl acetate extracts with water, dry over magnesium sulfate and evaporate to a residue comprising 3-oxo-17α-4-pregnene-21,17β-carbolactone. Purify via thin layer chromatography, developing the plate with chloroform/ethyl acetate (4:1) and eluting the portion containing the product with chloroform/ethyl acetate. Evaporate the chloroform/ethyl acetate solution to a residue comprising 3-oxo-17β-4-pregnene-21,17β-carbolactone, yield 10 mg. (50% theory); melting point 160°-162°C.

B. Alternatively, the compound of this example is prepared by treating 3β-hydroxy-17α-5-pregnene-21,17β-carbolactone with aluminum tri-tertiary butoxide in acetone with benzene in a manner similar to that described in Example VI-B. Isolate and purify the resultant product in a manner similar to that described in Example VIB to obtain 3-oxo-17α-4-pregnene-21,17β-carbolactone.

C.

3-Oxo-17α-19-nor-4-pregnene-21,17β-carbolactone

In a manner similar to that described in Example XI-A treat (17R)-spiro-[19-nor-4-androstene-17,1'-cyclobutane]-3,2'-dione with alkaline hydrogen peroxide in methanol and isolate the resultant product in a manner similar to that described to obtain 3-oxo-17α-19-nor-4-pregnene-21,17β-carbolactone.

EXAMPLE XII

3-OXO-17α-4,6-PREGNADIENE-21,17β-CARBOLACTONE AND THE 19-NOR ANALOG THEREOF

A. Treat 20 mg. of (17R)-spiro-[4,6-androstadiene-17,1'-cyclobutane]-3,2'-dione with 0.0048 ml. of hydrogen peroxide and 0.0086 ml. of 9 N sodium hydroxide in 0.5 ml. of methanol in a manner similar to that described in Example XI-A. Isolate and purify the resultant product in the manner described in Example XI-A to obtain 3-oxo-17α-4,6-pregnadiene-21,17β-carbolactone, yield 16 mg. (80% theory), melting point 159°-161°C.

B. In a manner similar to that described in Example XII-A treat (17R)-spiro-[19-nor-4,6-pregnadiene-17,1'-cyclobutane]-3,2'-dione with alkaline hydrogen peroxide in methanol. Isolate and purify the resultant compound in a manner similar to that described in Example XII-A to obtain 3-oxo-17α-19-nor-4,6-pregnadiene-21,17β-carbolactone.

EXAMPLE XIII

(17R)-SPIRO-[9α-FLUORO-11β-HYDROXY-4-ANDROSTENE-1,1'-CYCLOBUTANE]-3,2'-DIONE AND THE 1-DEHYDRO ANALOG THEREOF

A.
3-Ethoxy-9α-fluoro-11β-hydroxy-3,5-androstadiene-17-one

To 1 gm. of 9α-fluoro-11β-hydroxy-4-androstene-3,17-dione in a solution of 1 ml. of triethylorthoformate in 7 ml. of dioxane add 0.6 ml. of 5% concentrated sulfuric acid in dioxane. Stir at room temperature for five minutes then add 1 ml. of pyridine and evaporate in vacuo to a residue. Add cold ethanol and filter off the resultant precipitate comprising 3-ethoxy-9α-fluoro-11β-hydroxy-3,5-androstadiene-3,17-dione (0.8 gm.).

B.
(17R)-spiro-[3-ethoxy-9α-fluoro-11β-hydroxy-3,5-androstadiene-17,1'-cyclobutan]-2'-one To a suspension of cyclopropylidiphenylsulfonium tetrafluoroborate in dry dimethoxyethane (1 millimole in 10 ml.) cooled to −40°C add 1 millimole of dimsylsodium in dimethylsulfoixde then add 0.8 millimoles of 3-ethoxy-9α-fluoro-11β-hydroxy-3,5-androstadiene-17-one in 1 ml. of dimethoxyethane. Stir the reaction mixture at −40°C for five minutes, allow the reaction mixture to warm to room temperature then add 5 ml. of 1 molar aqueous fluoroboric acid. Extract the aqueous mixture with methylene chloride, wash the combined organic extracts with water, dry over magnesium sulfate and evaporate in vacuo to a residue comprising (17R)-spiro-[3-ethoxy-9α-fluoro-11β-hydroxy-3,5-androstadiene-17,1'-cyclobutan]-2'-one.

C.
(17R)-spiro-[9α-fluoro-11β-hydroxy-4-androstene-17,1'-cyclobutane]-3,2'-dione Dissolve the (17R)-spiro-[3-ethoxy-9α-fluoro-11β-hydroxy-3,5-androstadiene-17,1'-cyclobutan]-2'-one prepared in Example XIIIB in acetone containing 1 N hydrochloric acid. Allow the solution to stand for 30 minutes, then add pyridine until the solution is at about pH 7. Evaporate the solution in vacuo and dissolve the resultant residue in ethyl acetate. Wash the ethyl acetate solution with water, dry over magnesium sulfate and evaporate in vacuo to a residue comprising (17R)-spiro-[9α-fluoro-11β-hydroxy-4-androstene-17,1'-cyclobutane]-3,2'-dione.

D.
(17R)-spiro-[9α-fluoro-11β-hydroxy-4,6-androstadiene-17,1'-cyclobutane]-3,2'-dione In a manner similar to that described in Example VIII-B treat (17R)-spiro-[9α-fluoro-11β-hydroxy-4-androstene-17,1'-cyclobutane]-3,2'-dione with 1 molar equivalent of DDQ in 5% aqueous acetone at room temperature for 3 hours. Isolate and purify the resultant product in a manner similar to that described in Example VIII-B to obtain (17R)-spiro-[9α-fluoro-11β-hydroxy-4,6-androstadiene-17,1'-cyclobutane]-3,2'-dione.

EXAMPLE XIV

3-OXO-9α-FLUORO-11β-HYDROXY-17α-4-PREGNENE-21,17β-CAROBLACTONE AND THE 6-DEHYDRO ANALOG THEREOF

A. In a manner similar to that described in Example XI-A treat (17R)-spiro-[9α-fluoro-11β-hydroxy-4-androstene-17,1'-cyclobutane]-3,2'-dione with alkaline hydrogen peroxide in methanol. Isolate the resultant product in a manner similar to that described to obtain 3-oxo-9α-fluoro-11β-hydroxy-17α-4-pregnene-21,17β-carbolactone.

B. In similar manner treat (17-spiro-[9α-fluoro-11β-hydroxy-4,6-androstadiene-17,1'-cyclobutane]-3,2'-dione with alkaline hydrogen peroxide in methanol and isolate the resultant product in the manner described to obtain 3-oxo-9α-fluoro-11β-hydroxy-17α-4,6-pregnadiene-21,17β-carbolactone.

EXAMPLE XV

(17R)-SPIRO-[6β,7β-CYCLOMETHYLENE-4-ANDROSTENE-17,1'-CYCLOBUTANE]-3,2'-DIONE

A.
(17R)-Spiro-[2',2'-ethylenedixoy-3β-hydroxy-5-androstene-17,1'-cyclobutane]

Heat at reflux temperature for 3 hours a solution of (17R)-spiro-[3β-hydroxy-5-androstene-17,1'-cyclobutan]-2'-one in 2-methyl-2-ethyl-1,3-dioxolan (30 parts steroid to 600 parts of dioxolan) in the presence of para-toluene sulfonic acid (1 part to 30 parts steroid). Evaporate the solution in vacuo, dissolve the resultant residue in methylene chloride, wash the methylene chloride solution in water, dry over magnesium sulfate and evaporate in vacuo to a residue comprising (17R)-spiro-[2',2'-ethylenedioxy-3β-hydroxy-5-androstene-17,1'-cyclobutane].

B.
(17R)-Spiro-[2',2'-ethylenedioxy-4-androstene-17,1'-cyclobutan]-3-one

To a solution of (17R)-spiro-[2',2'-ethylenedioxy-3β-hydroxy-5-androstene-17,1'-cyclobutane] in acetone/benzene (1:2) add an equal weight of aluminum tri-tertiary butoxide. Heat at reflux temperature for 24 hours, pour into water, extract the aqueous solution with methylene chloride, wash the combined extracts with water, dry the methylene chloride solution over magnesium sulfate and evaporate in vacuo to a residue comprising (17R)-spiro-[2',2'-ethylenedioxy-4-androstene-17,1'-cyclobutan]-3-one.

C.
(17R)-Spiro-[2',2'-ethylenedioxy-4,6-androstadiene-17,1'-cyclobutan]-3-one To (17R)-spiro-[2',2'-ethylenedioxy-4-androstene-17,1'-cyclobutan]-3-one in tertiary butanol add an equal weight of chloranil and heat the mixture at reflux temperature for 24 hours. Cool to room temperature, filter, and evaporate the filtrate in vacuo to a residue. Dissolve the residue in methylene chloride wash the methylene chloride extracts with 1 N sodium hydroxide then with water, dry the methylene chloride extracts over magnesium sulfate then evaporate in vacuo to a residue comprising (17R)-spiro-[2',2'-ethylenedioxy-4,6-androstadiene-17,1'-cyclobutan]-3-one.

(17R)-Spiro-[2',2'-ethylenedioxy-6β,7β-cyclomethylene-4-androstene-17,1'-cyclobutan]-3-one To a solution of (17R)-spiro-[2',2'-ethylenedioxy-4,6-androstadiene-17,1'-cyclobutan]-3-one in dimethylsulfoxide add 1.1 equivalents of dimethyloxosulfonium methylide (generated from equimolar amounts of trimethylsulfoxonium iodide and sodium hydride in dimethylsulfoxide). Stir the reaction mixture at room temperature for 2 hours, then add water and extract the aqueous mixture with methylene chloride. Wash the combined methylene chloride extracts with water, dry over magnesium sulfate and evaporate in vacuo to a residue comprising (17R)-spiro-[2',2'-ethylenedioxy-6β,7β-cyclomethylene-4-androstene-17,1'-cyclobutan]-3-one in admixture with the 6α,7α-epimer thereof. Separate by chromatography on silica gel eluting with ether/hexane mixtures. Combine the like fractions of the 6β,7β-cyclomethylene derivative as determined by thin layer chromatography and evaporate to dryness and crystallize from acetone/hexane to obtain (17R)-spiro-[2',2'-ethylenedioxy-6β, 7β-cyclomethylene-4-androstene-17,1'-cyclobutan]-3-one.

E. To a solution of (17R)-spiro-[2',2'-ethylenedioxy-6β,7β-cyclomethylene-4-androstene-17,1'-cyclobutan]-3-one (100 mg.) in acetone (1 ml.), add para-toluenesulfonic acid (1 mg.) Heat at reflux temperature for 12 hours, then dilute with water, separate the resultant precipitate by filtration, dry the precipitate, then crystallize from acetone/hexane to obtain (17R)-spiro-[6β,7β-cyclomethylene-4-androstene-17,1'-cyclobutane]-3,2'-dione.

EXAMPLE XVI

3-OXO-6β,7β-CYCLOMETHYLENE-17α-4-PREGNENE-21,17β-CARBOLACTONE

In a manner similar to that described in Example IX treat (17R)-spiro-[6β,7β-cyclomethylene-4-androstene-17,1'-cyclobutane]-3,2'-dione in methanol with 30% hydrogen peroxide and aqueous sodium hydroxide. Isolate the resultant product in a manner similar to that described to obtain 3-oxo-6β,7β-cyclomethylene-17α-4-pregnene-21,17β-carbolactone.

EXAMPLE XVII (17R)-SPIRO-[7α-THIOACETYL-4-ANDROSTENE-17,1'-CYCLOBUTANE]-3,2'-DIONE, THE 19-NOR ANALOGS THEREOF AND THEIR 3-ETHOXY-3,5-ANDROSTADIENE ENOL ETHERS AND THE 9α-FLUORO-11β-HYDROXY DERIVATIVES OF THE FOREGOING

A.
(17R)-Spiro-[7α-thioacetyl-4-androstene-17,1'-cyclobutane]-3,2'-dione and the 9α-fluoro-11β-hydroxy derivative thereof 1. Add 1 gm. of (17R)-spiro-[4,6-androstadiene-17,1'-cyclobutane]-3,2'-dione to 1 ml. of thioacetic acid and heat the solution for ½ hour at 100°C. Evaporate the reaction mixture to a residue comprising (17R)-spiro-[7α-thioacetyl-4-androstene-17,1'-cyclobutane]-3,2'-dione. Purify by crystallization from ethyl acetate.

2. In a similar manner treat (17R)-spiro-[9α-fluoro-11β-hydroxy-4,6-androstadiene-17,1'-cyclobutane]-3,2'-dione with thioacetic acid at 100°C. Isolate and purify the resultant product in a manner similar to that described to obtain (17R)-spiro-[7α-thioacetyl-9α-fluoro-11β-hydroxy-4-androstene-17,1'-cyclobutane]-3,2'-dione.

3. Similarly, treat (17R)-spiro-[19-nor-4,6-androstadiene-17,1'-cyclobutane]-3,2'-dione in a manner similar to that described in Example XVII-A(1) to obtain (17R)-spiro-[7α-thioacetyl-19-nor-4-androstene-17,1'-cyclobutane]-3,2'-dione.

B.
(17R)-Spiro-[3-ethoxy-7α-thioacetyl-3,5-androstadiene-17,1'-cyclobutan]-2'-one 1. Dissolve the (17R)-spiro-[7α-thioacetyl-4-androstene-17,1'-cyclobutane]-3,2'-dione prepared in above Example XVII—A(1) in 5 ml. of dioxane and 0.5 ml. of absolute ethanol. Add a solution of 0.5 ml. of triethylorthoformate and 0.5 ml. of 1% concentrated sulfuric acid in dioxane. Allow the reaction mixture to stand at room temperature for 1 hour, then add 0.1 ml. of pyridine and evaporate the solution in vacuo. Dissolve the resultant residue in methylene chloride, wash the methylene chloride solution with water, dry over magnesium sulfate and evaporate in vacuo to a residue comprising (17R)-spiro-[3-ethoxy-7α-thioacetyl-3,5-androstadiene-17,1'-cyclobutan]-2'-one. Purify by crystallization from acetone/hexane to which a drop of pyridine has been added.

2. In a manner similar to that described in Example XVII-B(1) treat each of (17R)-spiro-[7α-thioacetyl-9α-fluoro-11β-hydroxy-4-androstene-17,1'-cyclobutane]-3,2'-dione and (17R)-spiro-[7α-thioacetyl-19-nor-4-androstene-17,1'-cyclobutane]-3,2'-dione in absolute ethanol with triethylorthoformate and 1% concentrated sulfuric acid in dioxane. Isolate and purify each of the resultant products in a manner similar to that described to obtain, respectively, (17R)-spiro-[3-ethoxy-7α-thioacetyl-9α-fluoro-11β-hydroxy-3,5-androstadiene-17,1'-cyclobutan]-2'-one and (17R)-spiro-[3-ethoxy-7α-thioacetyl-19-nor-3,5-androstadiene-17,1'-cyclobutan]-2'-one.

3. In similar manner, treat (17R)-spiro-[19-nor-4-androstene-17-1'-cyclobutane]-3,2'-dione with triethylorthoformate and sulfuric acid in dioxane and isolate the resultant product to obtain (17R)-spiro-[3-ethoxy-19-nor-3,5-androstadiene-17,1'-cyclobutan]-2'-one.

EXAMPLE XVIII (17R)-SPIRO-[1,4-ANDROSTADIENE-17,1'-CYCLOBUTANE]-3,2'-DIONES AND (17R)-SPIRO-[1,4,6-ANDROSTATRIENE-17,1'-CYCLOBUTANE]-3,2'-DIONES

A.
(17R)-Spiro-[1,4-androstadiene-17,1'-cyclobutane]-3,2'-dione

To 10 gm. of (17R)-spiro-[4-androstene-17,1'-cyclobutane]-3,2'-dione in 40 ml. of dry benzene and 40 ml. of dioxane add 16 gm. (3 mole equivalents) of 2,3-dicyano-5,6-dichlorobenzoquinone (DDQ) and heat at reflux temperature for 24 hours. Cool the reaction mixture, filter off the solid and evaporate the filtrate in vacuo at 40°C to a residue comprising (17R)-spiro-[1,4-androstadiene-17,1'-cyclobutane]-3,2'-dione. Purify by dissolving the residue in chloroform and filtering through 100 gm. of neutral alumina. Wash the alumina with copius amounts of chloroform. Evaporate the combined filtrates and crystallize the resultant residue from methanol to obtain (17R)-spiro-[1,4-androstadiene-17,1'-cyclobutane]-3,2'-dione.

B. In a manner similar to that described in above Example XVIII-A treat each of the following (17R)-spiro-[4-androstene-17,1'-cyclobutane]-3,2'-diones with DDQ in benzene and dioxane.

1. (17R)-spiro-[9α-fluoro-11β-hydroxy-4-androstene-17,1'-cyclobutane]-3,2'-dione,
2. (17R)-spiro-[4,6-androstadiene-17,1'-cyclobutane]-3,2'-dione,
3. (17R)-spiro-[9α-fluoro-11β-hydroxy-4,6-androstadiene-17,1'-cyclobutane]-3,2'-dione,
4. (17R)-spiro-[6β,7β-cyclomethylene-4-androstene-17,1'-cyclobutane]-3,2'-dione,
5. (17R)-spiro-[7α-thioacetyl-4-androstene-17,1'-cyclobutane]-3,2'-dione; and
6. (17R)-spiro-[7α-thioacetyl-9α-fluoro-11β-hydroxy-4-androstene-17,1'-cyclobutane]-3,2'-dione.

Isolate and purify each of the resultant products in a manner similar to that described in Example XVIII-A to obtain, respectively, 1. (17R)-spiro-[9α-fluoro-11β-hydroxy-1,4-androstadiene-17,1'-cyclobutane]-3,2'-dione,
2. (17R)-spiro-[1,4,6-androstatriene-17,1'-cyclobutane]-3,2'-dione,
3. (17R)-spiro-[9α-fluoro-11β-hydroxy-1,4,6-androstatrient-17,1'-cyclobutane]-3,2'-dione,
4. (17R)-spiro-[6β,7β-cyclomethylene-1,4-androstadiene-17,1'-cyclobutane]-3,2'-dione,
5. (17R)-spiro-[7α-thioacetyl-1,4-androstadiene-17,1'-cyclobutane]-3,2'-dione; and
6. (17R)-spiro-[7α-thioacetyl-9α-fluoro-11β-hydroxy-1,4-androstadiene-17,1'-cyclobutane]-3,2'-dione.

EXAMPLE XIX

CONVERSION OF 3-HYDROXY-17α-PREGNANE-21,17β-CARBOLACTONES TO 3-OXO-17α-4,6-PREGNADIENE-21,17β-CARBOLACTONE

A. 3-Oxo-5α,17α-Pregnane-21,17β-carbolactone

1. Dissolve 2 gm. of 3β-hydroxy-5α,17α-pregnane-21,17β-carbolactone in 100 ml. of acetone and add slightly more than 1 equivalent of 8 N chromic acid solution. Stir the reaction mixture at room temperature for 30 minutes, then dilute with a large excess of water. Filter the resultant precipitate, wash the precipitate with water and dry to obtain 3-oxo-5α,17α-pregnane-21,17β-carbolactone.

2. In similar manner treat each of the following with chromic acid in acetone.

1. 3α-hydroxy-5α,17α-pregnane-21,17β-carbolactone,
2. 3α-hydroxy-5β,17α-pregnane-21,17β-carbolactone,
3. 3β-hydroxy-5β,17α-pregnane-21,17β-carbolactone.

Isolate and purify each of the resultant products to obtain respectively, 1. 3-oxo-5α,17α-pregnane-21,17β-carbolactone,
2. 3-oxo-5β,17α-pregnane-21,17β-carbolactone,
3. 3-oxo-5β,17α-pregnane-21,17β-carbolactone.

B. 2,4-Dibromo-3-oxo-5α,17α-pregnane-21,17β-carbolactone

To 0.5 gm. of 3-oxo-5α,17α-pregnane-21,17β-carbolactone in 15 ml. of dioxane at room temperature add 0.32 ml. of bromine in 3 ml. of acetic acid. Allow the reaction mixture to stand at room temperature for 20 hours, then pour into water, filter off the resultant precipitate, wash the precipitate with water and dry at room temperature to obtain 2,4-dibromo-3-oxo-5α,17α-pregnane-21,17β-carbolactone.

In similar manner treat 3-oxo-5β,17α-pregnane-21,17β-carbolactone with bromine in dioxane to obtain 2,4-dibromo-3-oxo-5β,17α-pregnane-21,17β-carbolactone.

C. 3-Oxo-17α-4,6-pregnadiene-21,17β-carbolactone

To 2,4-dibromo-3-oxo-5α,17α-pregnane-21,17β-carbolactone in 25 ml. of dimethylacetamide add 1 gm. of lithium bromide and 1 gm. of sodium sulfate. Stir the reaction mixture at 60°C for 18 hours. Pour into water, filter the resultant precipitate, wash the precipitate with water and dry to obtain 3-oxo-17α-4,6-pregnadiene-21,17β-carbolactone. Purify by chromatography on silica gel eluting with chloroform:ethyl acetate (100:1).

In similar manner treat 2,4-dibromo-3-oxo-5β,17α-pregnane-21,17β-carbolactone with lithium bromide in dimethylacetamide. Isolate and purify the resultant product in a manner similar to that described to obtain 3-oxo-17α-4,6-pregnadiene-21,17β-carbolactone.

EXAMPLE XX

CONVERSION OF 3-HYDROXY-17α-19-NOR-PREGNANE-21,17β-CARBOLACTONE TO 3-OXO-17α-19-NOR-4-PREGNENE-21,17β-CARBOLACTONE

A. In a manner similar to that described in Example XIX-A treat

3β-hydroxy-5α,17α-19-nor-pregnane-21,17β-carbolactone with chromic acid in acetone. Isolate and purify the resultant product in a manner similar to that described to obtain 3-oxo-5α,17α-19-nor-pregnane-21,17β-carbolactone.

In a similar manner treat each of the following with chromic acid in acetone.

1. 3β-hydroxy-5β,17α-19-nor-pregnane-21,17β-carbolactone,
2. 3α-hydroxy-5α,17α-19-nor-pregnane-21,17β-carbolactone,
3. 3α-hydroxy-5β,17α-19-nor-pregnane-21,17β-carbolactone.

Isolate and purify each of the resultant products in a manner similar to that described to obtain, respectively, 1. 3-oxo-5β,17α-19-nor-pregnane-21,17β-carbolactone,
2. 3-oxo-5α,17α-19-nor-pregnane-21,17β-carbolactone,
3. 3-oxo-5β,17α-19-nor-pregnane-21,17β-carbolactone.

B. 3-Oxo-17α-19-nor-4-pregnene-21,17β-carbolactone

To 3-oxo-5α,17α-19-nor-pregnane-21,17β-carbolactone in benzene add 1 molar equivalent of DDQ and heat at reflux temperature for 48 hours. Cool the reaction mixture, filter off the solid and evaporate the filtrate to a residue comprising 3-oxo-17α-19-nor-4-pregnene-21,17β-carbolactone. Purify by dissolving the residue in chloroform and filtering the chloroform solution through a short column of neutral alumina washing copiously with chloroform. Evaporate the combined chloroform washings and fractionally crystallize the resultant residue from methanol to obtain purified 3-oxo-17α-19-nor-4-pregnene-21,17β-carbolactone.

In similar manner 3-oxo-5β, 17α-nor-pregnane-21,17β-carbolactone, upon treatment with DDQ in benzene, is converted to 3-oxo-17α-19-nor-4-pregnene-21,17β-carbolactone.

I claim:

1. A compound selected from the group consisting of a 3-oxo-4-androstene-17-spirocyclobutanone of the following formula I:

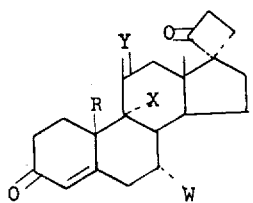

wherein R is a member selected from the group consisting of hydrogen and methyl; and
W is a member selected from the group consisting of hydrogen and acetylthio;
X and Y are both hydrogen, or X is fluorine and Y is (H,βOH) provided R is methyl;
the 1-dehydro analogs thereof when R is methyl;
the 6-dehydro analogs thereof when W is hydrogen;
the 1,6-bis-dehydro analogs thereof when R is methyl and W is hydrogen;
and a 3-oxo-4-androstene-17-spirocyclobutanone of the following formula II:

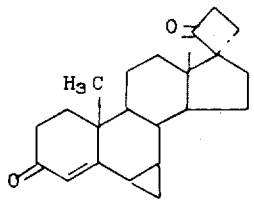

and the 1-dehydro analog thereof.

2. A compound of claim 1, formula I, wherein R is methyl and W is acetylthio.

3. A compound of claim 1, formula I, wherein R is methyl and W is hydrogen.

4. The 4-dehydro compound of claim 1, formula I, wherein R is methyl and W, X and Y are hydrogen, said compound being (17R)-spiro-[4-androstene-17,1'-cyclobutane]-3,2'-dione.

5. The 4,6-bis-dehydro compound of claim 1, formula I, wherein R is methyl and W, X and Y are hydrogen, said compound being (17R)-spiro-[4,6-androstadiene-17,1'-cyclobutane]-3,2'-dione.

6. A compound selected from the group consisting of a 3-hydroxy-5ξ-androstane-17-spirocyclobutanone of the following formula:

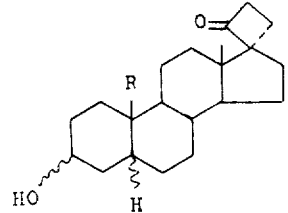

wherein R is a member selected from the group consisting of hydrogen and methyl;
the 5-dehydro analogs thereof when R is methyl;
the 3-lower alkoxy-3,5-bis-dehydro derivatives thereof;
the 3-lower alkoxy-7α-acetylthio-3,5-bis-dehydro derivatives thereof;
the 3-lower alkoxy-9α-fluoro-11β-hydroxy-3,5-bis-dehydro derivatives thereof when R is methyl;
the 3-lower alkoxy-7α-acetylthio-9α-fluoro-11β-hydroxy-3,5-bis-dehydro derivatives thereof when R is methyl; and
the 5(10)-dehydro analog thereof and the 3-lower alkoxy-2,5(10)-bis-dehydro derivatives thereof when R is hydrogen.

7. The 3β-hydroxy-5α compound of claim 6 wherein R is methyl, said compound being (17R)-spiro-[3β-hydroxy-5α-androstane-17,1'-cyclobutan]-2'-one.

8. The 3β-hydroxy-5-dehydro compound of claim 6 wherein R is methyl, said compound being (17R)-spiro-[3β-hydroxy-5-androstene-17,1'-cyclobutan]-2'-one.

9. The 3,5-bis-dehydro compound of claim 6 wherein R is methyl, said compound being (17R)-spiro-[3-lower alkoxy-3,5-androstadiene-17,1'-cyclobutan]-2'-one.

10. The 3-ethoxy compound of claim 9, said compound being (17R)-spiro-[3-ethoxy-3,5-androstadiene-17,1'-cyclobutan]-2'-one.

11. The process for the preparation of a compound selected from the group consisting of 3-hydroxy-androstane-17-spiro cyclobutanone of following formula I:

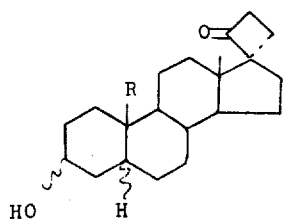

wherein R is a member selected from the group consisting of hydrogen and methyl;
the 5-dehydro analogs thereof when R is methyl;
the 3-lower alkoxy-3,5-bis-dehydro derivatives thereof;
the 3-lower alkoxy-9α-fluoro-11β-hydroxy-3,5-bis-dehydro derivatives thereof when R is methyl; and
the 5(10)-dehydro analog thereof and the 3-lower alkoxy-2,5(10)-bis-dehydro derivatives thereof when R is hydrogen,
which comprises the reaction of a compound selected from the group consisting of a 17-oxoandrostane of following formula A:

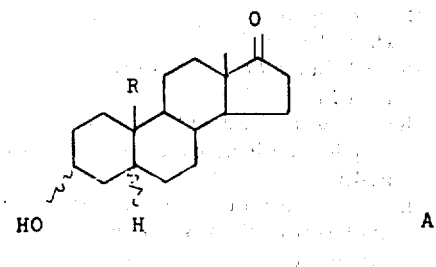

A

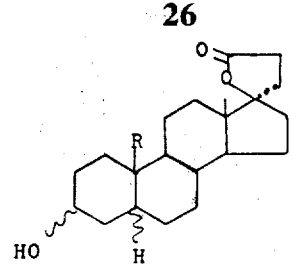

II wherein R is a member selected from the group consisting of hydrogen and methyl;
  the 5-dehydro analogs thereof when R is methyl;
  the 3-lower alkoxy-3,5-bis-dehydro derivatives thereof;
  the 3-lower alkoxy-9α-fluoro-11β-hydroxy-3,5-bis-dehydro derivatives thereof when R is methyl; and
  the 5(10)-dehydro analog thereof and the 3-lower alkoxy-2,5(10)-bis-dehydro derivatives thereof when R is hydrogen,
with a reagent containing an arylsulfurcyclopropane grouping selected from the group consisting of a cyclopropylaryl sulfide and a cyclopropylarylsulfonium salt having a non-nucleophilic anion in an organic solvent together with a strong base;
followed by the treatment in situ of the intermediate thereby formed with a member selected from the group consisting of an aqueous acid and, when said reagent is a cyclopropylarylsulfonium salt, with water.

12. The process of claim 11 wherein said reagent is cyclopropylphenylsulfide, said organic solvent is tetrahydrofuran, said strong base is butyl lithium, and said intermediate thereby formed is treated with aqueous fluoroboric acid.

13. The process of claim 11 wherein said reagent is N,N-dimethylaminocyclopropylphenyloxosulfonium fluoroborate, said solvent is dimethylsulfoxide, and said strong base is sodium hydride.

14. The process of claim 13 wherein the intermediate thereby formed is treated with aqueous fluoroboric acid.

15. The process of claim 11 wherein said reagent is diphenylcyclopropylsulfonium fluoroborate, said organic solvent is dimethylsulfoxide and said strong base is potassium hydroxide.

16. The process of claim 15 wherein said intermediate thereby formed is treated with water.

17. The process of claim 15 wherein said intermediate thereby formed is treated with aqueous fluoroboric acid.

18. The process of claim 11 wherein said reagent is diphenylcyclopropylsulfonium fluoroborate, said organic solvent is glyme and said strong base is dimsylsodium.

19. The process of claim 11 wherein said reagent is diphenylcyclopropylsulfonium fluoroborate, said organic solvent is tert-butanol and said strong base is potassium tert-butoxide.

20. The process of claim 11 including the subsequent step of the reaction of the 3-hydroxy-androstane-17-spirocyclobutanone thereby formed with a Baeyer-Villager oxidation reagent to form a steroidal 17β-carbolactone of the following formula II:

wherein R is a member selected from the group consisting of hydrogen and methyl;
  the 5-dehydro analogs thereof when R is methyl;
  the 3-lower alkoxy-3,5-bis-dehydro derivatives thereof;
  the 3-lower alkoxy-9α-fluoro-11β-hydroxy-3,5-bis-dehydro derivatives thereof when R is methyl; and
  the 3-lower alkoxy-2,5(10)-bis-dehydro derivatives thereof when R is hydrogen.

21. The process of claim 20 wherein said 3-hydroxy-androstane-17-spirocyclobutanone is (17R)-spiro-[3β-hydroxy-5-androstene-17,1'-cyclobutan]-2'-one and said Baeyer-Villager reagent is alkaline hydrogen peroxide; whereby is formed 3β-hydroxy-17α-[5-pregnene]-21,17β-carbolactone.

22. The process for the preparation of a steroidal carbolactone of following formulae I and II:

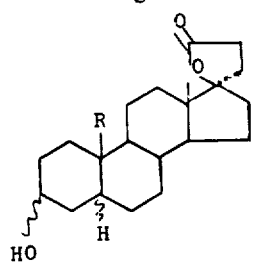

I and

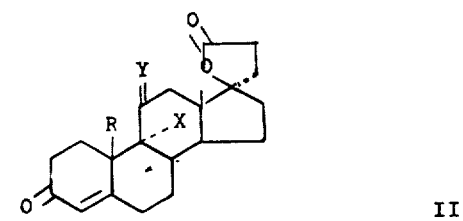

II wherein R is a member selected from the group consisting of hydrogen and methyl;
  X and Y are both hydrogen, or X is fluorine and Y is (H,βOH) provided R is methyl;
  the 5-dehydro analogs of the compounds of formula I when R is methyl;
  the 3-lower alkoxy-3,5-bis-dehydro derivatives of formula I;
  the 5(10)-dehydro analog thereof and the 3-lower alkoxy-2,5(10)-bis-dehydro of formula I provided R is hydrogen;
  the 6-dehydro analogs of formula II;
  the 1-dehydro and 1,6-bis-dehydro analogs of formula II when R is methyl;
  the 6β7β-cyclomethylene derivatives of formula II when R is methyl and X and Y are hydrogen, and the 1-dehydro analog thereof;
  which comprises the reaction of a steroidal 17-spirocyclobutanone selected from the group consisting of a 3-hydroxy-5α-androstane of formula III and a 3-oxo-4-dehydroandrostane of formula IV:

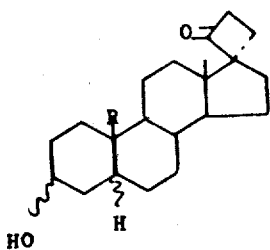

and

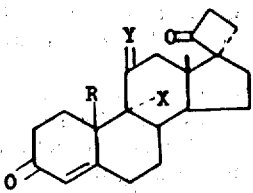

wherein R, X and Y are as hereinabove defined;

the 5-dehydro analogs of compounds of formula III when R is methyl;

the 3-lower alkoxy-3,5-bis-dehydro analogs of formula III;

the 3-lower alkoxy-9α-fluoro-11β-hydroxy-3,5-bis-dehydro derivatives of formula III when R is methyl;

the 5(10)-dehydro analog and the 3-lower alkoxy-2,5(10)-bis-dehydro analogs of formula III when R is hydrogen;

the 6-dehydro analogs of formula IV;

the 1-dehydro and 1,6-bis-dehydro analogs of formula IV when R is methyl; and the 6,6₂,7β-cyclomethylene derivative of formula IV when R is methyl and X and Y are hydrogen, and the 1-dehydro analog thereof;

with a Baeyer-Villager oxidation reagent.

23. The process of claim 22 wherein said Baeyer-Villager reagent is alkaline hydrogen peroxide.

* * * * *